United States Patent
Kerr et al.

[11] Patent Number: 5,213,764
[45] Date of Patent: May 25, 1993

[54] METERING DEVICE FOR SLIDE ANALYSIS SYSTEM

[75] Inventors: Alexander F. Kerr, Yorktown; Edwin H. Mernyk, North Tarrytown, both of N.Y.; George E. Zabetakis, Bethel, Conn.; Uri Escoli, Teaneck, N.J.; Georges Revillet, Onex; Andre Nicole, Choulex, both of Switzerland

[73] Assignee: Miles Inc., Tarrytown, N.Y.

[21] Appl. No.: 700,240

[22] Filed: May 15, 1991

[51] Int. Cl.$^5$ ............................................. B01L 3/02
[52] U.S. Cl. ........................................ 422/100; 422/63; 436/46; 436/54; 436/180; 73/864.14; 73/864.75
[58] Field of Search ............... 422/100, 63; 436/46, 436/54, 180; 73/864.14, 864.24, 864.25

[56] References Cited

U.S. PATENT DOCUMENTS

| | | | |
|---|---|---|---|
| 4,737,344 | 4/1988 | Koizumi et al. | 73/864.24 |
| 4,785,677 | 11/1988 | Higo | 73/864.14 |
| 5,055,263 | 10/1991 | Meltzer | 422/100 |
| 5,055,408 | 10/1991 | Higo et al. | 422/100 |

FOREIGN PATENT DOCUMENTS 0021434 2/1985 Japan ............................. 73/864.25

Primary Examiner—Lynn M. Kummert
Attorney, Agent, or Firm—Jeffrey M. Greenman

[57] ABSTRACT

The metering device for a slide analysis system deposits serum onto a slide that is held in a spotting position by a slide transfer device. The metering device is movable to a sampling position relative to a slide holding module to aspirate serum from a serum source on a slide cartridge in the slide holding module and is also movable to a spotting position to spot serum on the slide held by the slide transfer device. The metering device also has rotational as well as elevational movement and includes a built-in pipette tip ejector for discarding a used pipette tip.

7 Claims, 16 Drawing Sheets

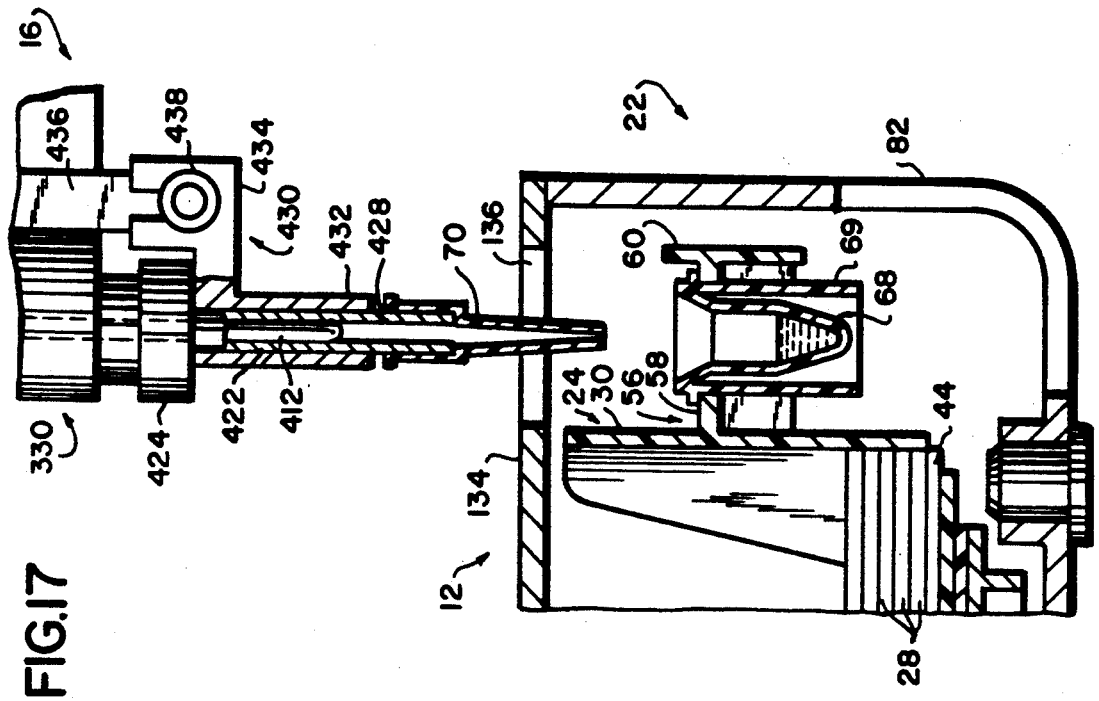
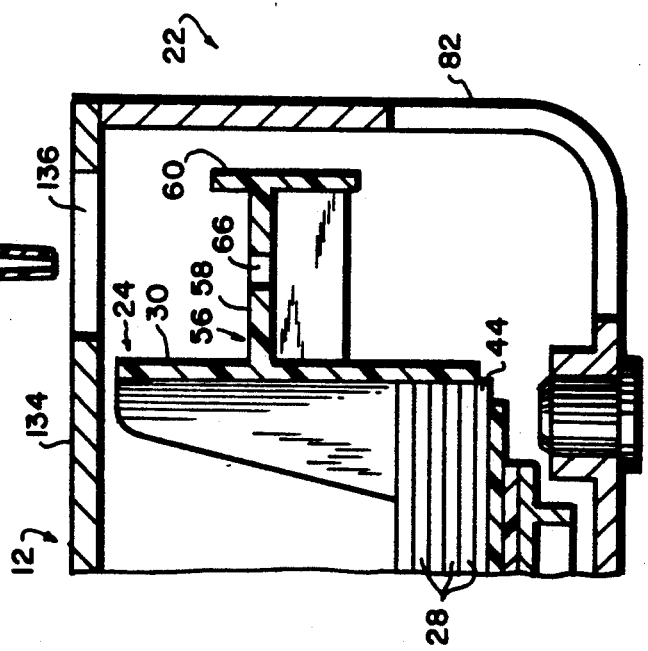

METERING DEVICE FOR SLIDE ANALYSIS SYSTEM

BACKGROUND OF THE INVENTION

This invention relates to systems for automatic analysis of blood samples and more particularly to a dispensing device for spotting a slide with biological fluid such as blood.

Apparatus for analyzing biological fluid samples such as blood usually include dispensers or metering devices to deposit blood or other fluid samples on a slide for subsequent analysis.

For example, U.S. Pat. Nos. 4,568,549; 4,512,952; 4,296,069 and 4,296,070 disclose systems and system components for automatic analysis of blood samples deposited on slides. Included in such systems is a fluid spotting device which spots the slides with a fluid sample.

U.S. Pat. Nos. 4,452,899 and 4,675,301 show a fluid spotting head that automatically moves up and down as well as back and forth and carries a disposable pipette tip. A pipette tip ejection structure for removing the pipette tip from the spotting device is spaced and separate from the spotting head. Thus the pipette tip ejection structure is not built into the spotting head and the spotting head must be brought into alignment with the ejection structure in order to eject the pipette tip.

It is thus desirable to provide a metering or spotting device for a slide analysis system which accesses blood samples from a first location such as a slide holding device, spots the slides with the accessed sample and has a built-in pipette tip ejector for automatically ejecting a used pipette tip when the testing of an individual fluid sample is completed.

OBJECTS AND SUMMARY OF THE INVENTION

Among the several objects of the invention may be noted the provision of a novel metering device for a slide analysis system, a novel metering device that accesses a fluid sample at one location and spots a slide at another location, and a novel slide spotting device with provision for automatic ejection of a pipette tip.

Other objects and features of the invention will be in part apparent and in part pointed out hereinafter.

In accordance with the present invention, a metering device is provided for spotting a slide with serum prior to analysis of the slide. The metering device includes a metering body that has a first elevated position wherein the metering body is at rest, a first descended position wherein the metering body aspirates serum from a sample container, another descended position wherein the metering body dispenses serum from a pipette tip onto a slide and a further descended position wherein the metering body can automatically eject a pipette tip by means of a built-in pipette tip ejector mechanism. The metering body can also self-install a new pipette tip after a used pipette tip has been ejected.

In addition to vertical movement, the metering body has angular movement wherein it is swung to a first location for installation of a pipette tip onto the metering body. The metering body can also be swung from the first location to a sampling position wherein the newly installed pipette tip is aligned with a sample container.

The metering body lowers the pipette tip into the sample container for aspiration of serum from the sample container and then rises or elevates for further angular rotation into a spotting position for spotting fluid onto a slide. While in the spotting position, the metering body is oriented in substantial alignment with an incubator slot in an incubator module.

The metering body, when it dispenses or spots serum onto the slide, descends slightly to position the pipette tip in close proximity to the slide.

When the pipette tip on the metering body is no longer needed it can be ejected by a built-in pipette tip ejector. After the pipette tip is ejected the metering body can be repositioned at the first location for installation of a new pipette tip and further aspiration of serum from a new sample container.

The invention accordingly comprises the constructions hereinafter described, the scope of the invention being indicated in the claims.

BRIEF DESCRIPTION OF THE DRAWINGS

In the accompanying drawings,

FIGS. 14–16 are enlarged fragmentary elevational views showing the metering module prior to and after installation of a pipette tip from a slide cartridge in the slide holding module; and FIGS. 17–19 are enlarged fragmentary sectional views showing the metering module prior to, during and after aspiration of serum from a sample cup in the slide holding module.

Corresponding reference characters indicate corresponding parts throughout the several views of the drawings.

DETAILED DESCRIPTION OF THE INVENTION

Figure 1:
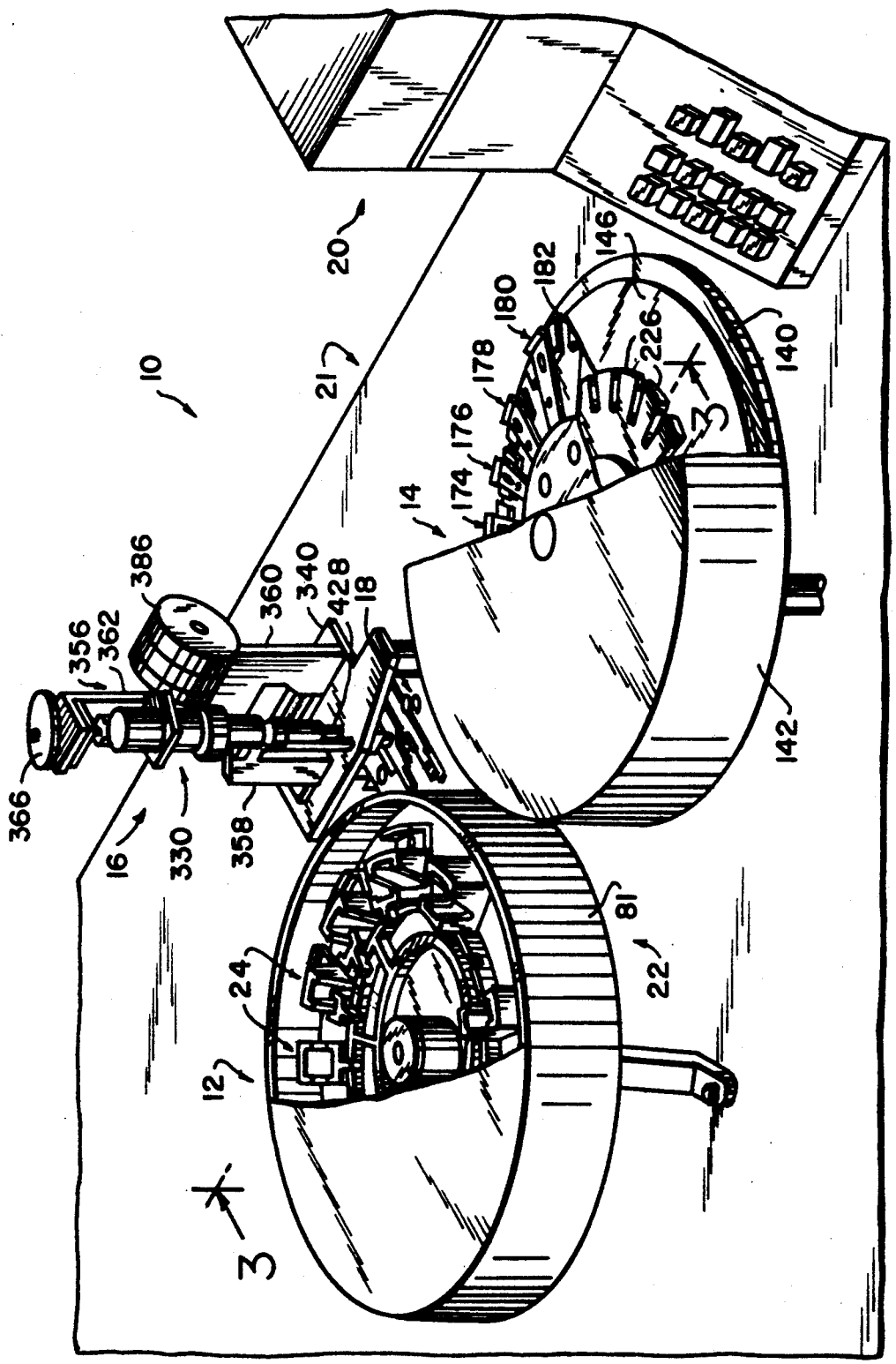
FIG. 1 is a perspective view of a slide analysis system having a metering device incorporating one embodiment of the invention.

A slide analysis system incorporating one embodiment of the metering device is generally indicated by the reference number 10 in FIG. 1.

The system 10 includes a slide holding module 12, an incubator module 14 spaced from the slide holding module 12, and a depositing or metering module 16 for spotting slides with a predetermined amount of serum or fluid, spaced from the slide holding module 12 and the incubator module 14.

The system 10 further includes a slide transfer mechanism 18, also referred to as a pick and place device, arranged below the metering module 16, and a computer control 20 for programming and controlling the operations of the slide analysis system 10. A table top or desk 21 supports the system 10.

The slide holding module 12 includes a generally cylindrical housing 22 that contains a plurality of slide cartridges 24. The slide cartridges 24 are radially spaced around the inside of the housing 22 and detachably seated therein.

Figure 6:
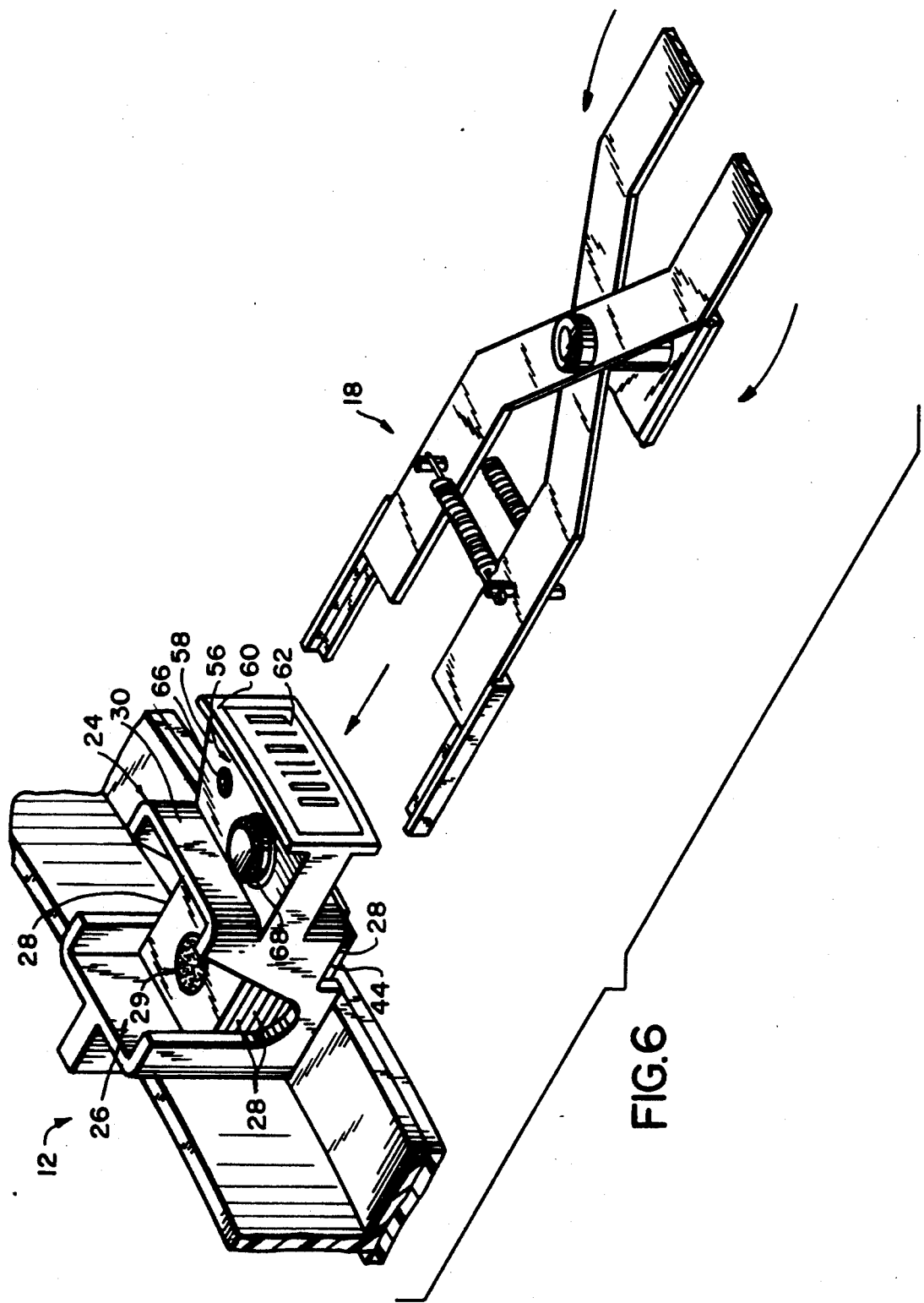
FIG. 6 is an enlarged fragmentary perspective view of the slide transfer device prior to removal of a slide from a slide cartridge in the slide holding module.
Figure 7:
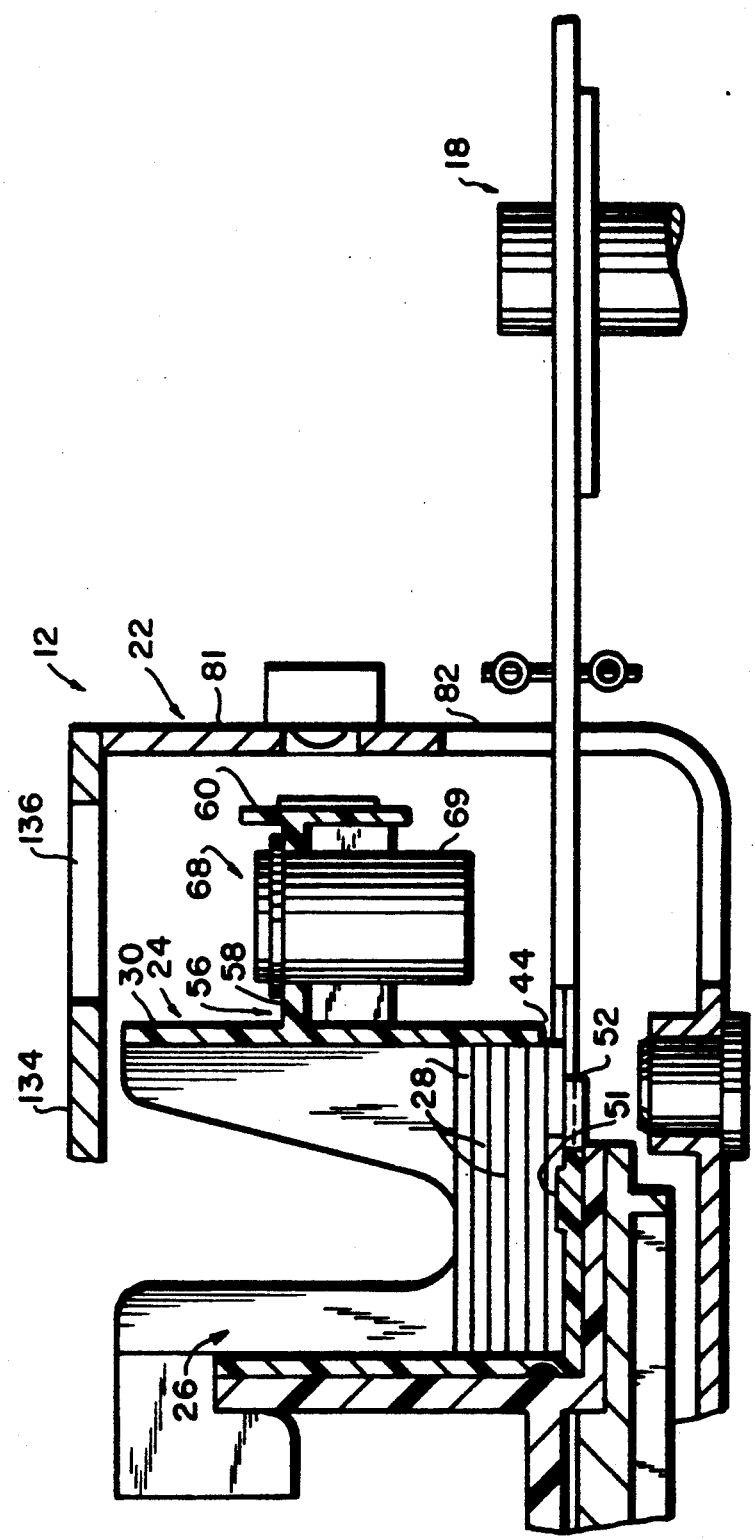
FIG. 7 is an enlarged fragmentary sectional view of the slide transfer device engaged with a slide in the slide cartridge.

Referring to FIGS. 1, 6 and 7, the slide cartridge 24 includes a slide compartment 26 for accommodating a stack of generally rectangular slides 28.

Figure 4:
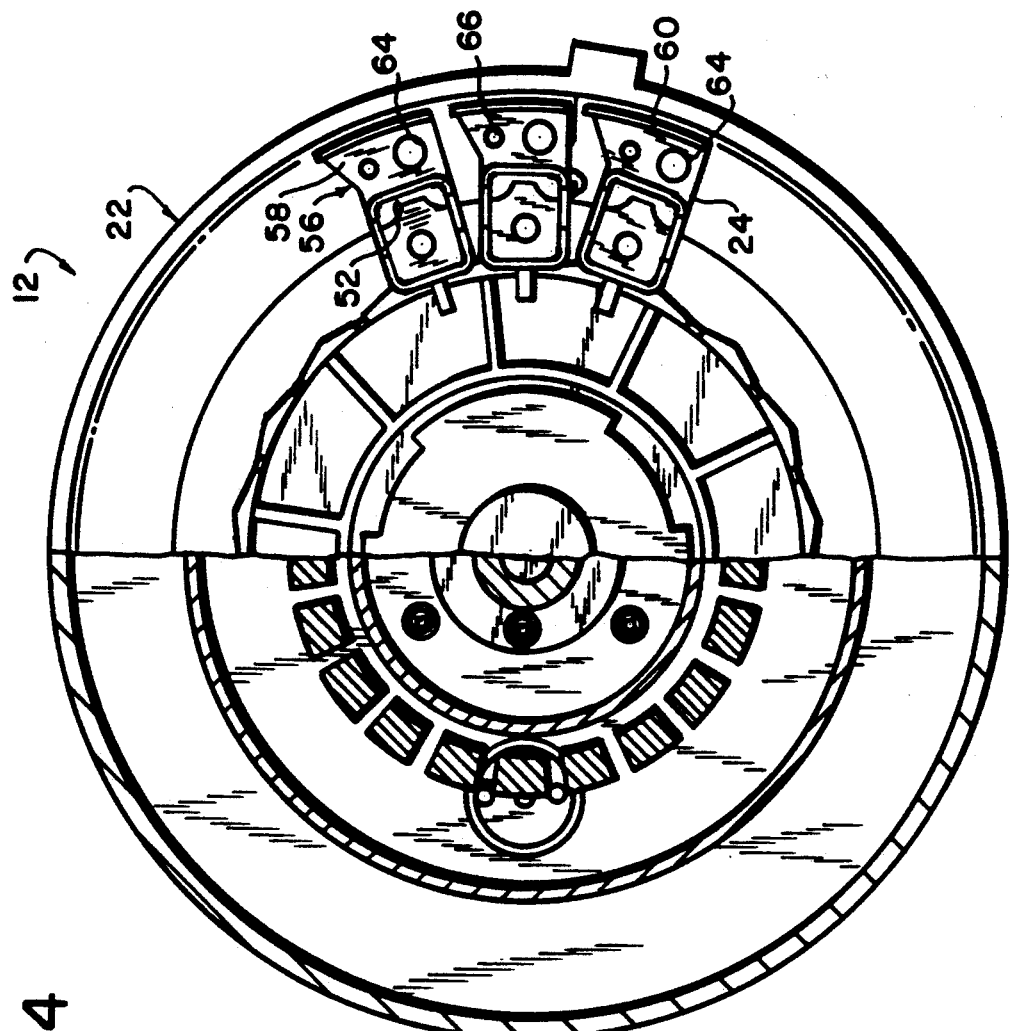
FIG. 4 is a simplified plan view partly shown in section of a slide holding module within the system.
Figure 15:
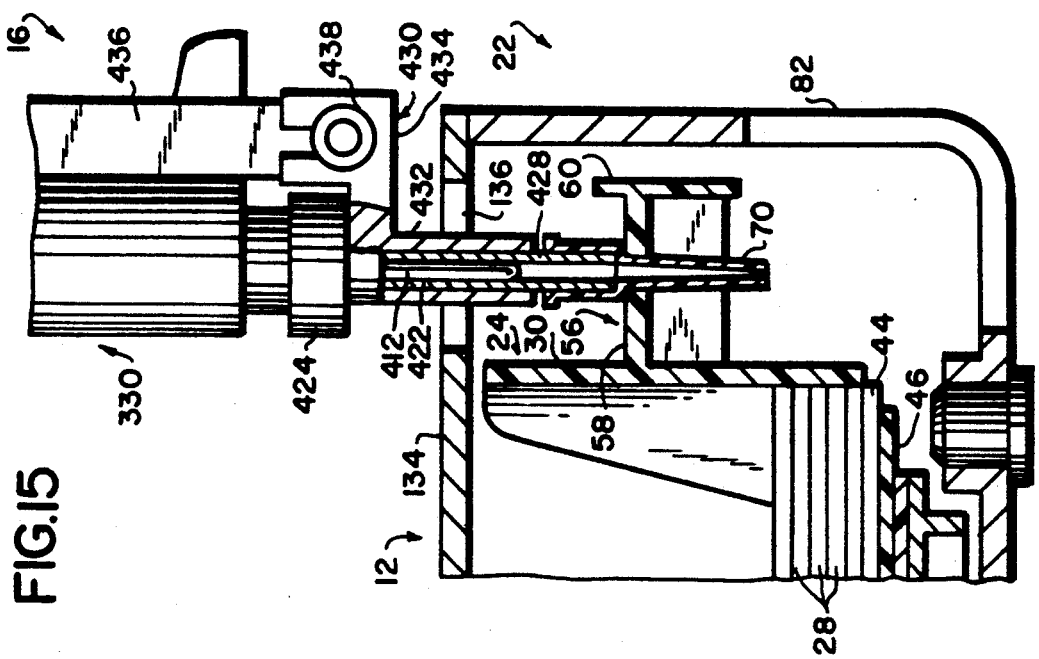
Figure 14:
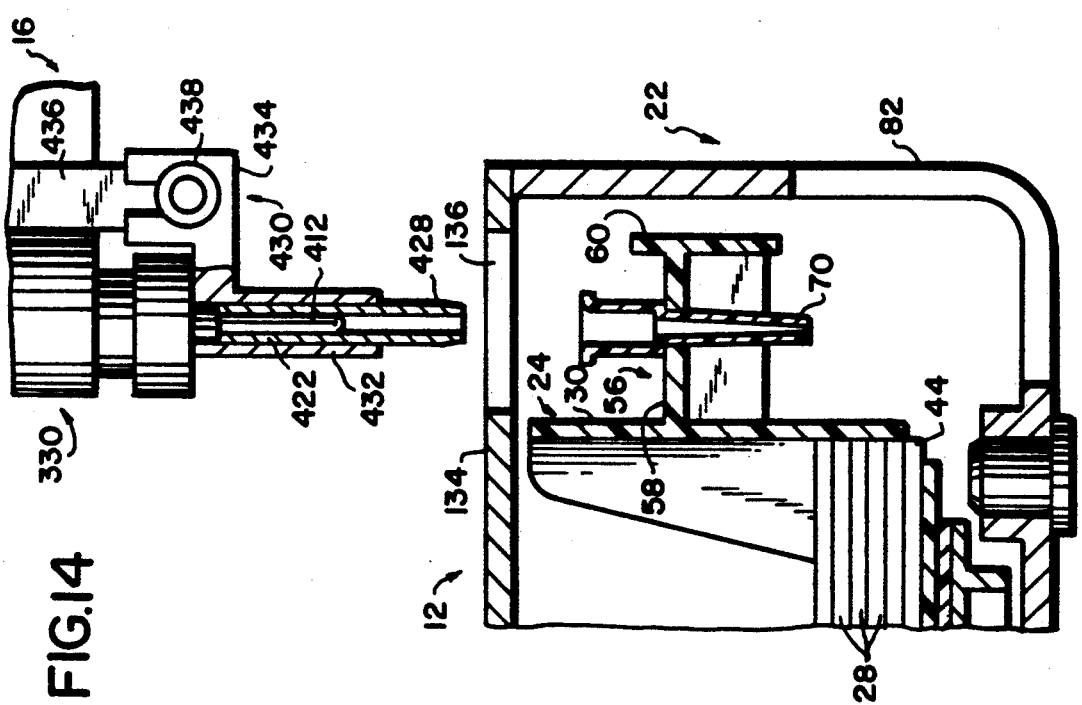

Referring to FIG. 6, a shelf-like appendage 56 is formed on a front wall 30 of the slide cartridge 24 and includes a shelf portion 58 and a data wall 60. The shelf portion 58 is formed with a relatively large opening 64 (FIG. 4) and a relatively small opening 66. The opening 64 detachably accommodates a graduated sample container 68 (FIGS. 6 and 17-19) that contains serum or fluid to be analyzed. The sample container 68 is formed with a cylindrical retainer shell 69 and the shell and cup are collectively referred to as the sample container 68. The opening 66 detachably accommodates a disposable pipette tip 70 (FIGS. 14-16).

A cover piece 134 (FIG. 1) is provided on the slide holding module 12 and includes an opening 136 (FIGS. 7 and 14-19) that permits access to the sample container 68 and the pipette tip 70.

The slide holding module 12 thus accommodates, for example, twenty slide cartridges 24. Each of the slide cartridges 24 corresponds to a particular individual and contains a separate pipette tip 70 and a separate sample container 68 containing the serum sample that corresponds to a particular individual. Identification of the cartridge 24 with a particular individual is accomplished by means of the data slip 62 provided on the wall portion 60 of the cartridge 24. The number of slides 28 held by the cartridge 24 determines the number of tests to be performed on the serum sample.

Figure 3:
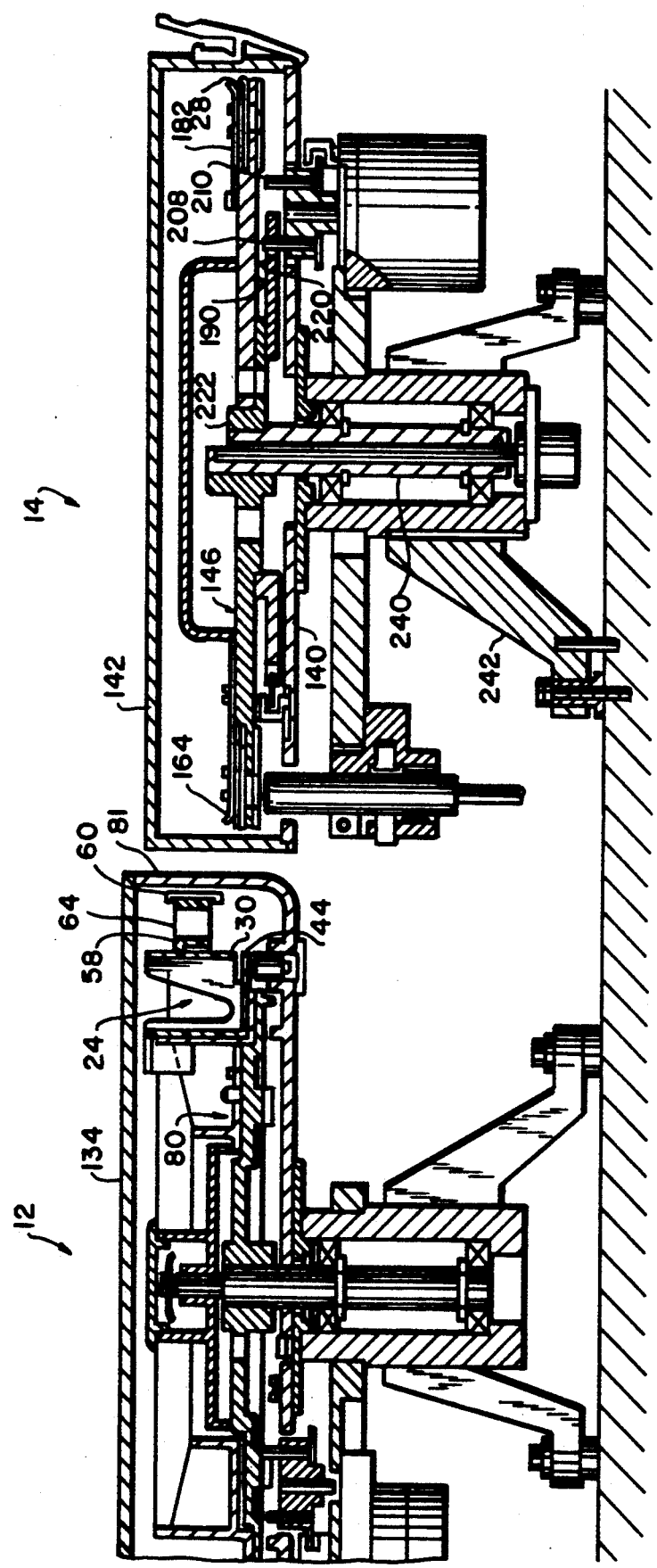
FIG. 3 is a sectional view taken on the line 3—3 of FIG. 1.

When all the slides in a particular cartridge 24 have been removed for test purposes, a rotatable cartridge tray 80 (FIG. 3) within the slide holding module 12 is rotated a predetermined amount to enable the next sequential cartridge 24 to be located at a slide withdrawal position wherein a slide removal slot 44 in a cartridge 24 aligns with an external slide withdrawal slot 82 (FIGS. 4 and 7) formed in an annular wall 81 of the slide holding module housing 22.

Figure 5:
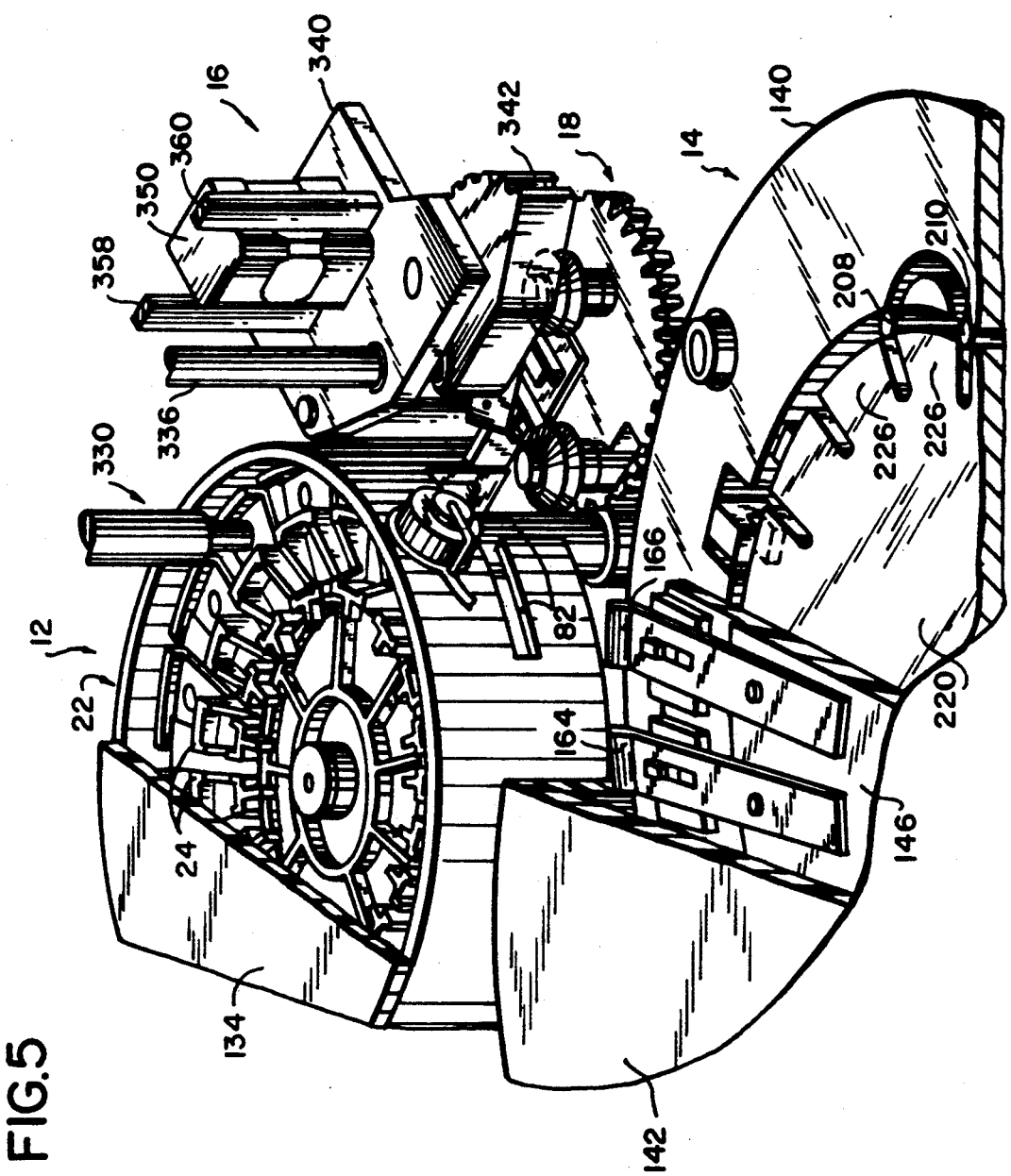
FIG. 5 is an enlarged fragmentary perspective view of system components shown in FIG. 1.

Referring to FIGS. 1 and 5, the incubator module 14, which is of generally cylindrical shape, includes a circular base plate 140 and a cup-shaped cover member 142 detachably secured to the base plate 140. A slot 145 (FIG. 2) is formed in the cover member 142 through which slides 28 are inserted or withdrawn from the incubator module 14.

Referring to FIGS. 1 and 5, the incubator module 14 also includes a cam plate 220 affixed to a hub 222 at an underside 190 of a slide holding tray 146 such that the hub 222, the cam plate 220 and the slide holding tray 146 rotate in unison with a shaft 240. The cam plate 220 includes spaced peripheral cam-like teeth 226 (FIG. 5) that are engaged in succession by the actuating pins 208, 210 to cause incremental rotation of the slide holding tray 146.

The incubator module shaft 240 supports the slide holding tray 146 and extends through the base plate 140 from a fixed pedestal 242.

Figure 2:
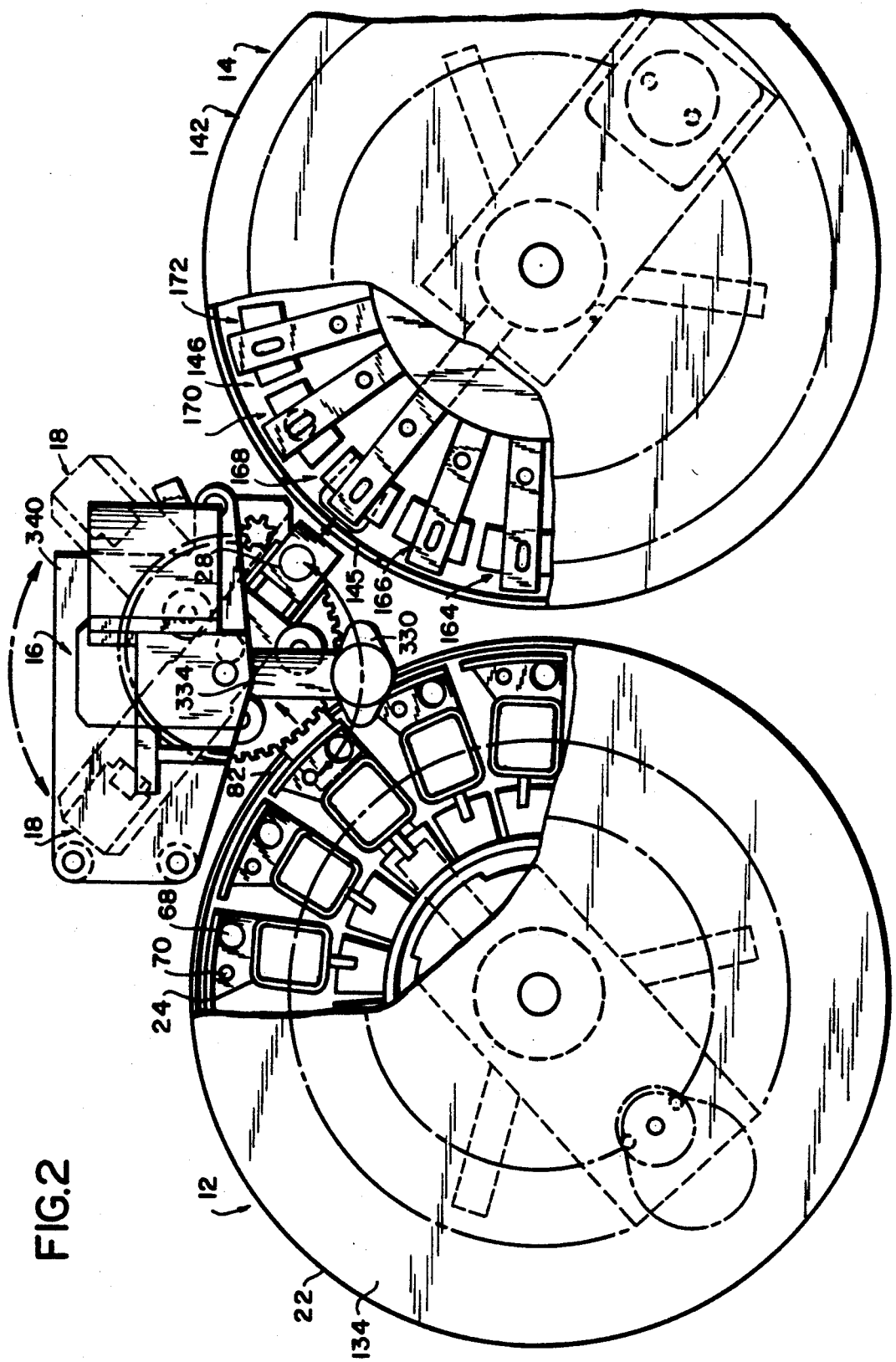
FIG. 2 is a plan view thereof.

Slides 28 are individually inserted into the incubator module 14 through the slot 145 (FIG. 2). For example, when a slide 28 has been spotted with serum and is inserted into the incubator module 14 at a slide retainer station 168, the incubator slide holding tray 146 will rotate in a counterclockwise direction, as viewed in FIG. 2, to align a next slide retainer station 170 with the slot 145. The slide retainer station 170 is thus ready to receive the next slide 28. As each slide retainer station 164-182 receives the slide, the slide holding tray 146 automatically rotates a predetermined incremental amount to permit a next sequential slide retainer station to align with the incubator slot 145 for installation of a freshly spotted slide 28.

Figure 8:
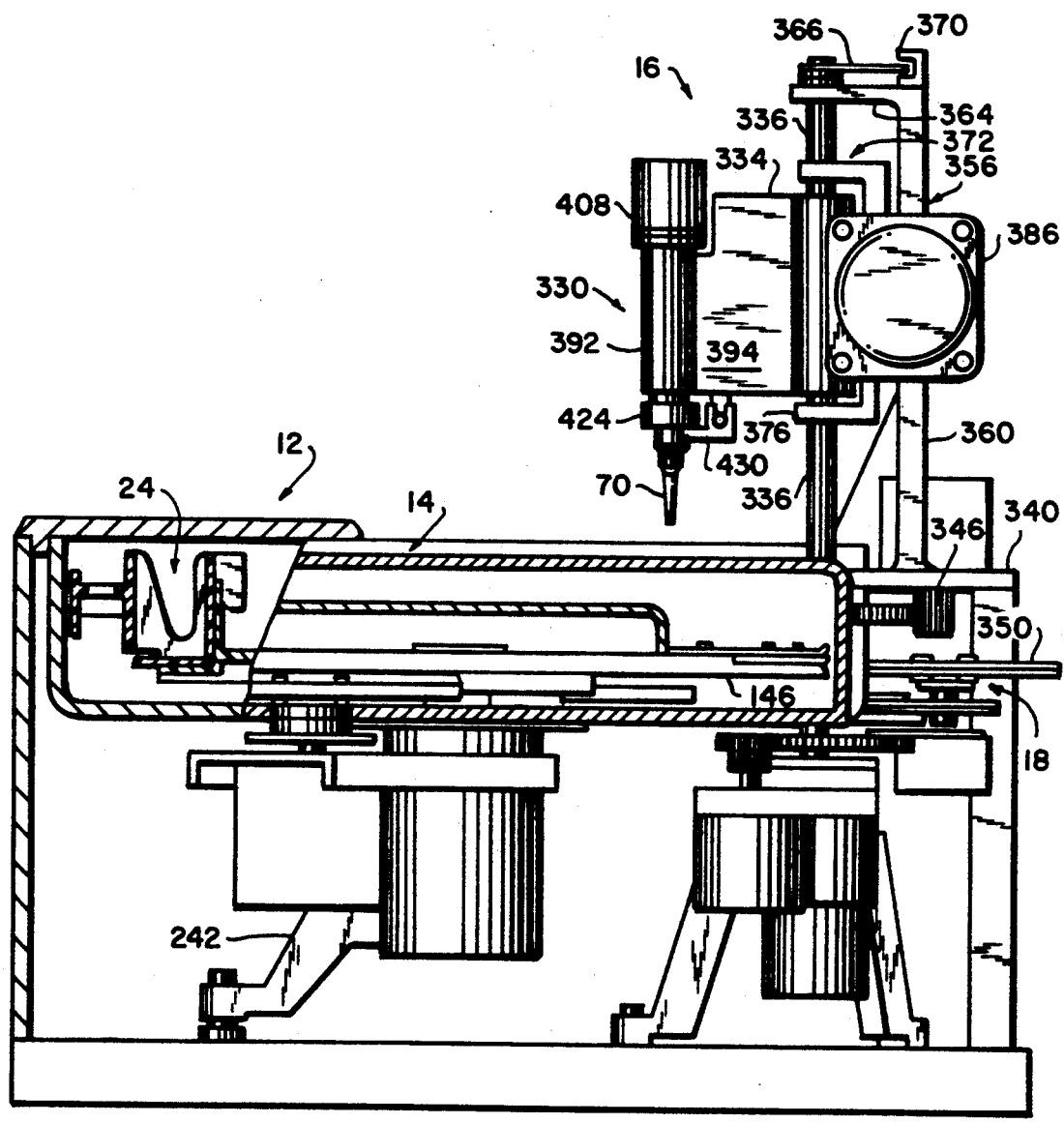
FIG. 8 is a side elevational view of the slide holding module and metering module partly shown in section.

Referring to FIG. 8, the depositing or metering module 16 for spotting slides 28 includes a metering body 330 having a frame extension 334 that is axially slidable on a shaft 336.

Figure 9:
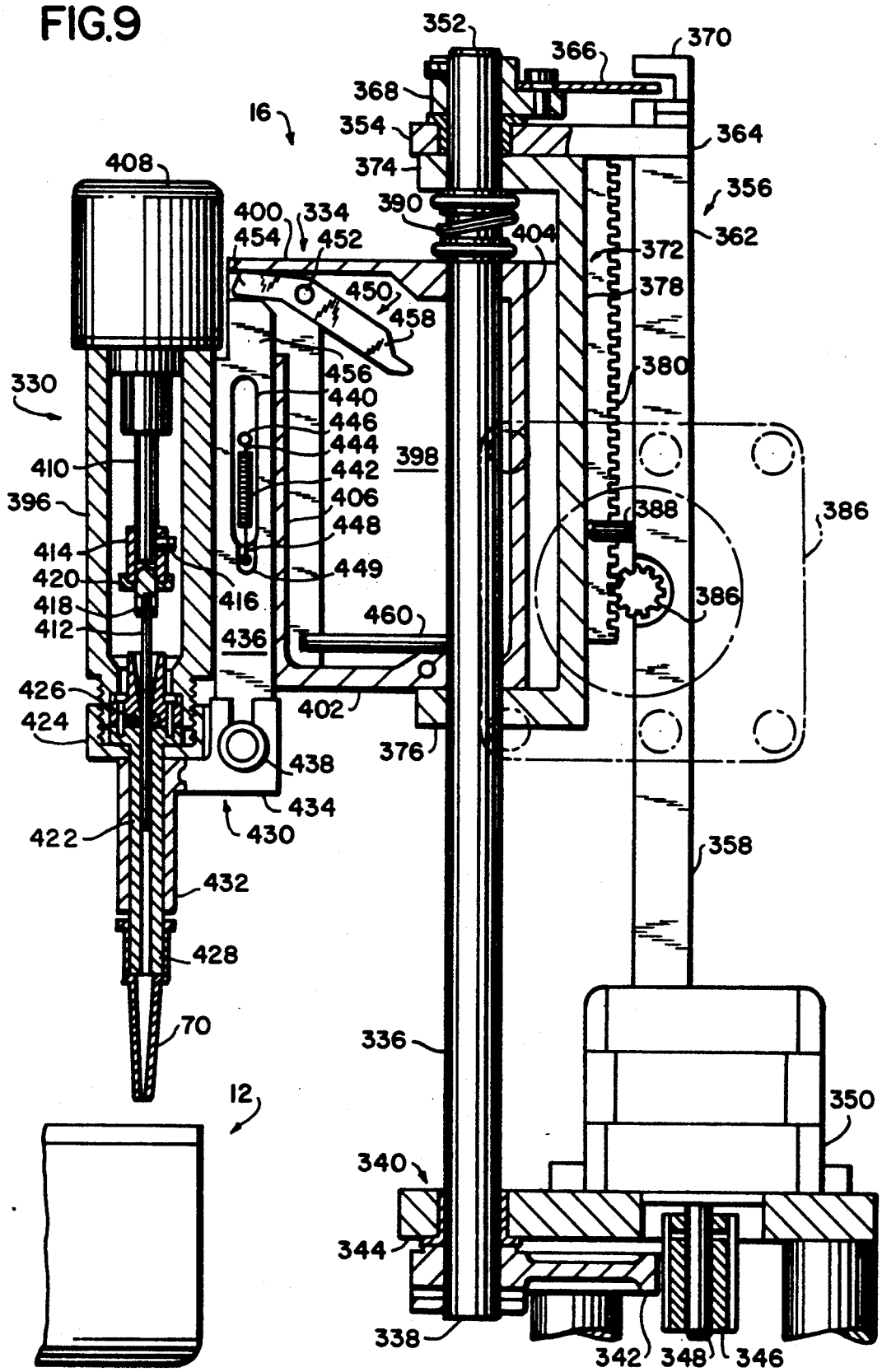
FIG. 9 is an elevational view of the metering module.

Referring to FIG. 9, the shaft 336 has an end portion 338 rotatably mounted in and extending below a base plate 340. Transfer means for moving the metering body 330 toward and away from the slide holding module 12 and to other positions such as a metering location for depositing serum onto a slide 28 include a sector gear 342. The sector gear 342 is fixed to an end portion 338 of the shaft 336 below an underside 344 of the base plate 340. The sector gear 342 is driven by a pinion gear 346 fixed to a shaft 348 of a motor 350 mounted on the base plate 340.

An opposite end portion 352 of the shaft 336 is rotatably supported in an arm 354 of a support frame 356 having spaced legs 358 and 360 (FIG. 1) mounted on the base plate 340. A trunk portion 362 of the support frame 356 extends from the legs 358 and 360, and includes an end portion 364 that joins the arm 354 (FIG. 23). Under this arrangement, rotation of the pinion 346 causes rotation of the sector gear 342, which rotates the shaft 336 to swing the metering body 330 from one selectable position to another selectable position such as, for example, from the position of FIG. 23 to the position of FIG. 24.

A flag member 366 (FIG. 9) is provided at the shaft end portion 352, being affixed to a holding collar 368 that is fastened to the end portion 352. A sensor device 370 is arranged on the arm 354 to sense angular movement of the flag member 366 based on rotational movement of the shaft 336.

Referring again to FIG. 9, a yoke member 372 having upper and lower arms 374 and 376 is slidably mounted to the shaft 336. The yoke member 372 further includes a back portion 378 that joins the arms 374 and 376. The back portion 378 is formed with or otherwise supports a rack 380. The rack 380 engages a pinion 382 driven by a bi-directional motor 386 supported on the trunk portion 362 of the support frame 356. One or more pins 388 extending from the trunk portion 362 are arranged to slightly touch the back portion 378 to prevent rotation of the frame 334 with respect to the shaft 336, without interfering with slidable movement of the frame 334 with respect to the shaft 336.

Referring to FIG. 9, the frame 334 is biased against the arm 376 of the yoke member 372 by a dampening spring 390. The dampening spring 390 is provided on the shaft 336 between the arm 374 and the frame 334 thus spacing the frame 334 from the arm 374.

When the motor 386 causes the pinion 382 to rotate in a counterclockwise direction as viewed in FIG. 9, the rack 380 moves in a downward direction with the yoke member 372, thus urging downward movement of the frame 334 and the metering body 330. The dampening spring 390 assures a smooth transfer of movement from the yoke member 372 to the frame 334.

Figure 18:
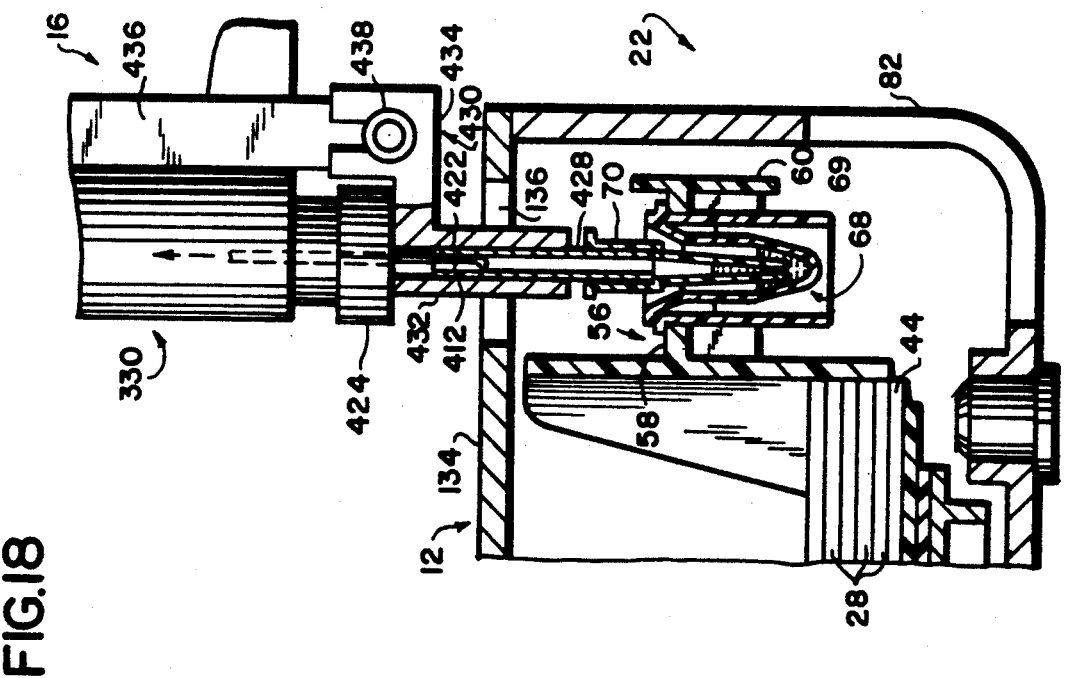

Downward movement of the metering body 330 is needed during installation of a pipette tip 70 to the metering body as shown in FIGS. 14 and 15, and for the purpose of aspiration of fluid into the pipette tip 70 from the sample container 68 as shown in FIGS. 17 and 18. Downward movement of the metering body is also needed for the purpose of spotting a slide 28 as shown in FIG. 10.

Figure 10:
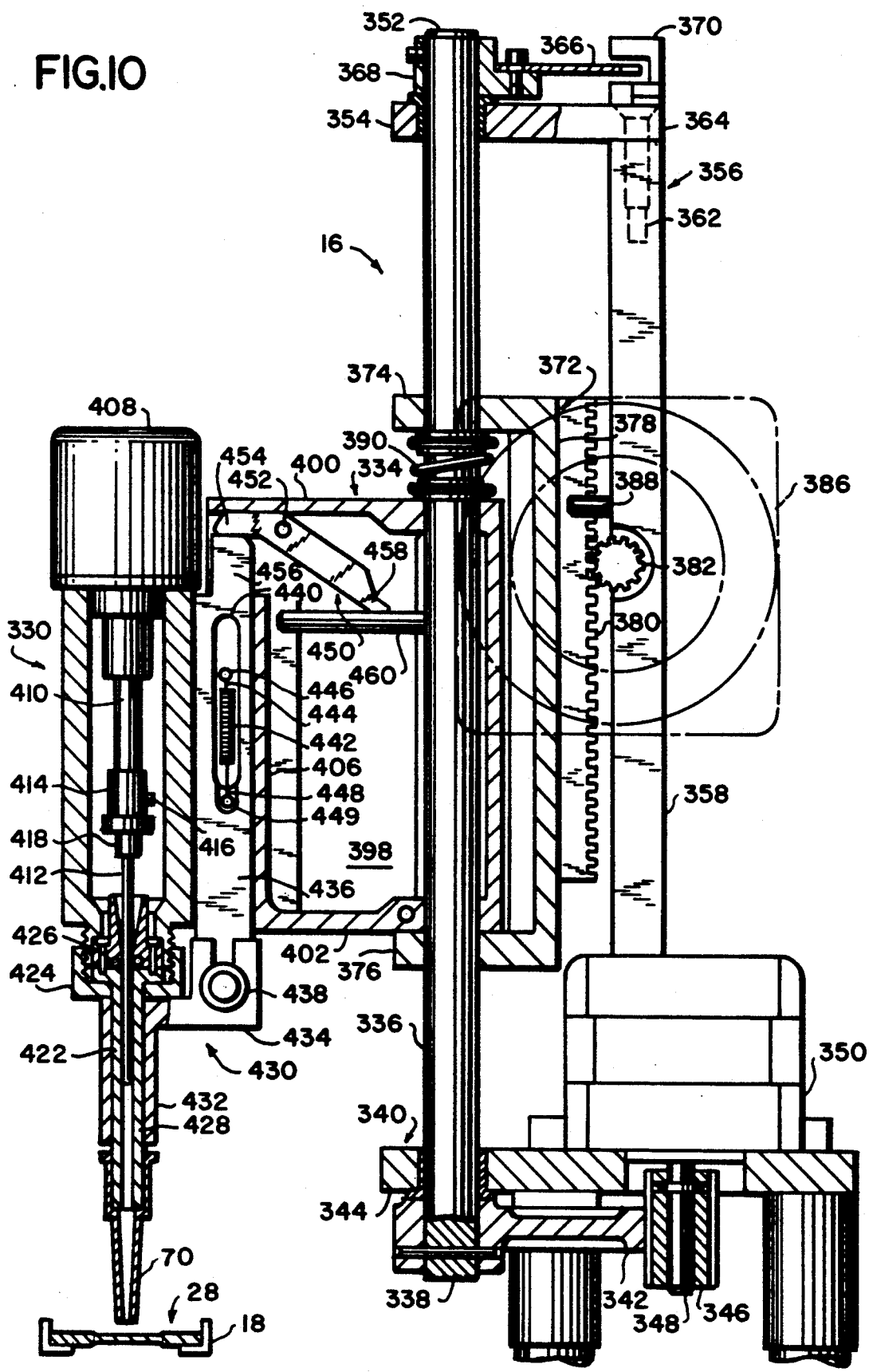
FIG. 10 is an elevational view, similar to FIG. 9, of the metering module during slide spotting.
Figure 11:
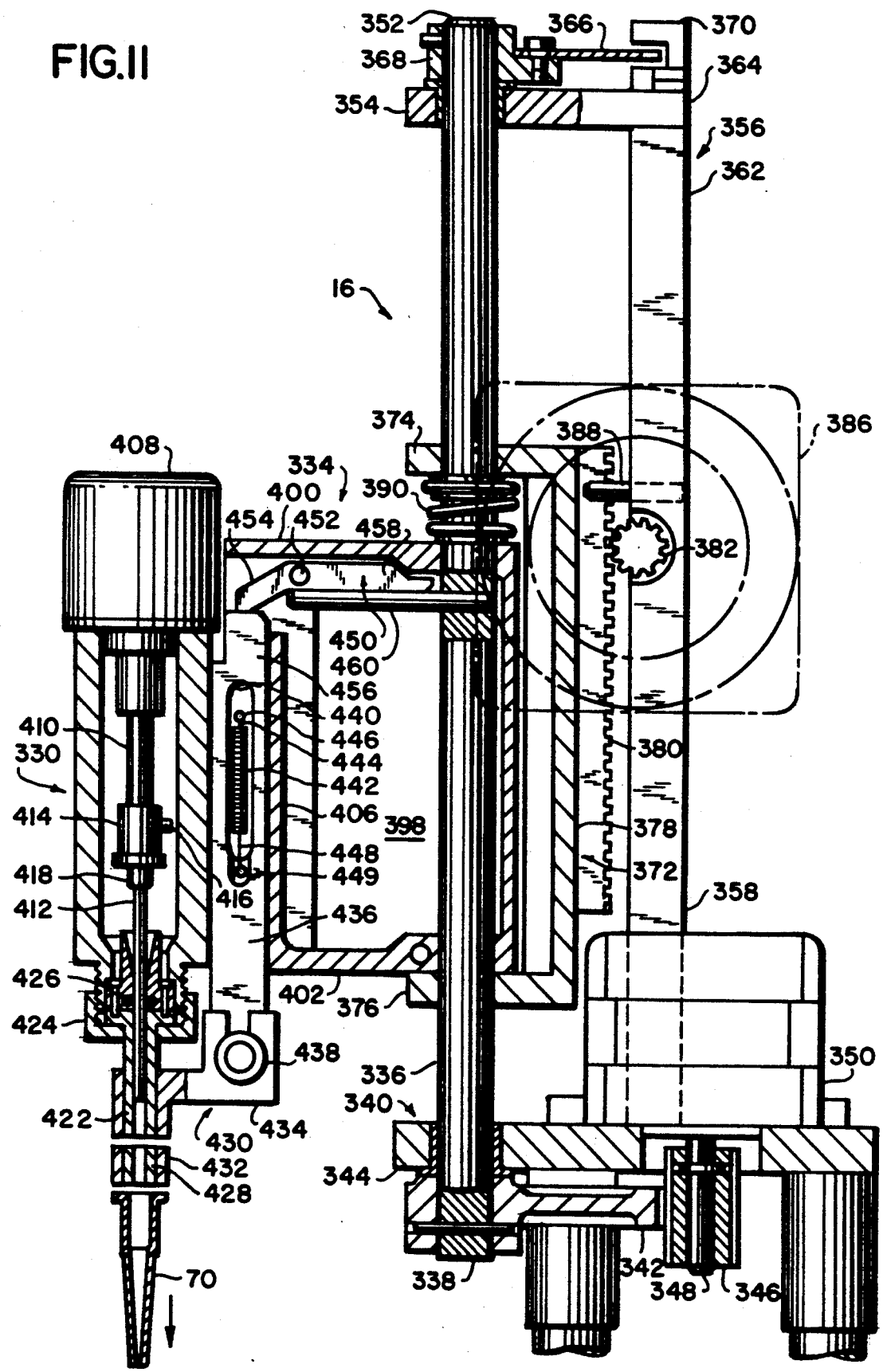
FIG. 11 is an elevational view similar to FIG. 10 of the metering module during ejection of a pipette tip.
Figure 19:
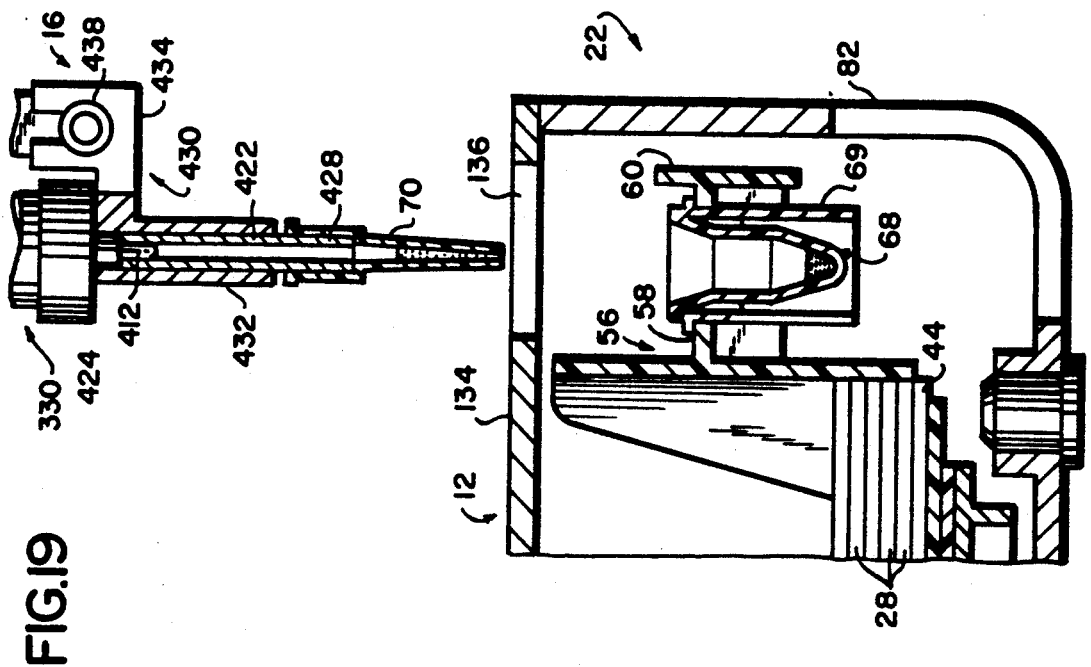

Upward movement of the metering body 330 is accomplished by rotation of the pinion 382 in a clockwise direction as viewed in FIGS. 10 and 11. Clockwise movement of the pinion 382 causes the rack 380 and yoke 372 to move in an upward direction relative to the shaft 336, thereby urging the frame 334 and the metering body 330 to move in an upward direction. Upward movement of the metering body 330 is needed to elevate the metering body 330 from the slide holding module 12 after a pipette tip 70 has been installed on the metering body 330 as shown in FIGS. 15 and 16. Upward movement of the metering body 330 is also needed after the pipette tip 70 has aspirated fluid from the sample container 68 as shown in FIGS. 18 and 19. The upper limit of movement for the metering body 330 is the rest position shown in FIG. 9. The metering body 330 returns to the rest position after it has moved downwardly for the purpose of installation of a pipette tip 70, aspiration of serum from a sample container 68, spotting of a slide 28 and automatic ejection of a pipette tip 70.

Figure 12:
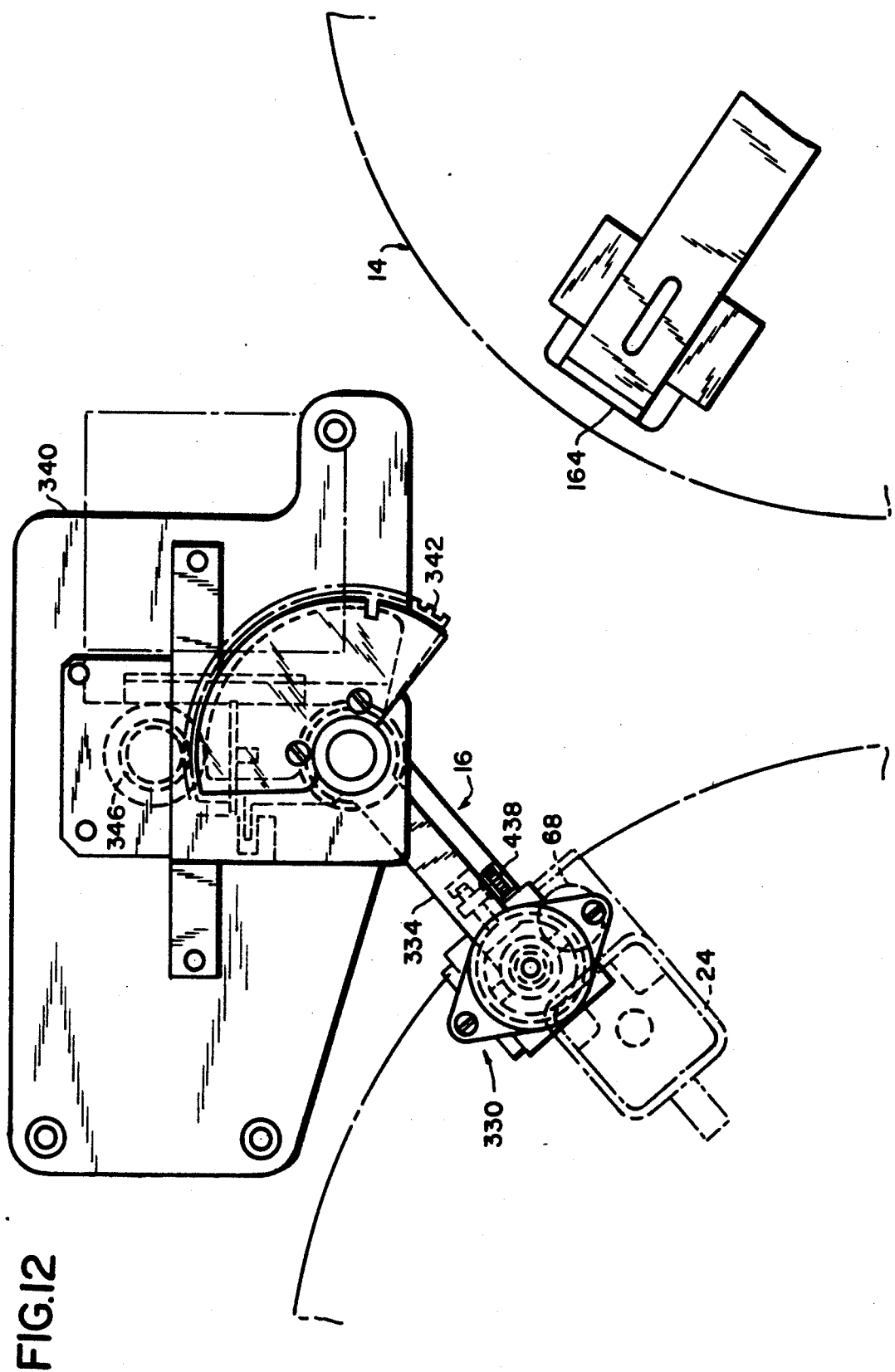
FIG. 12 is a simplified fragmentary plan view of the metering module in a pipette installation position.
Figure 13:
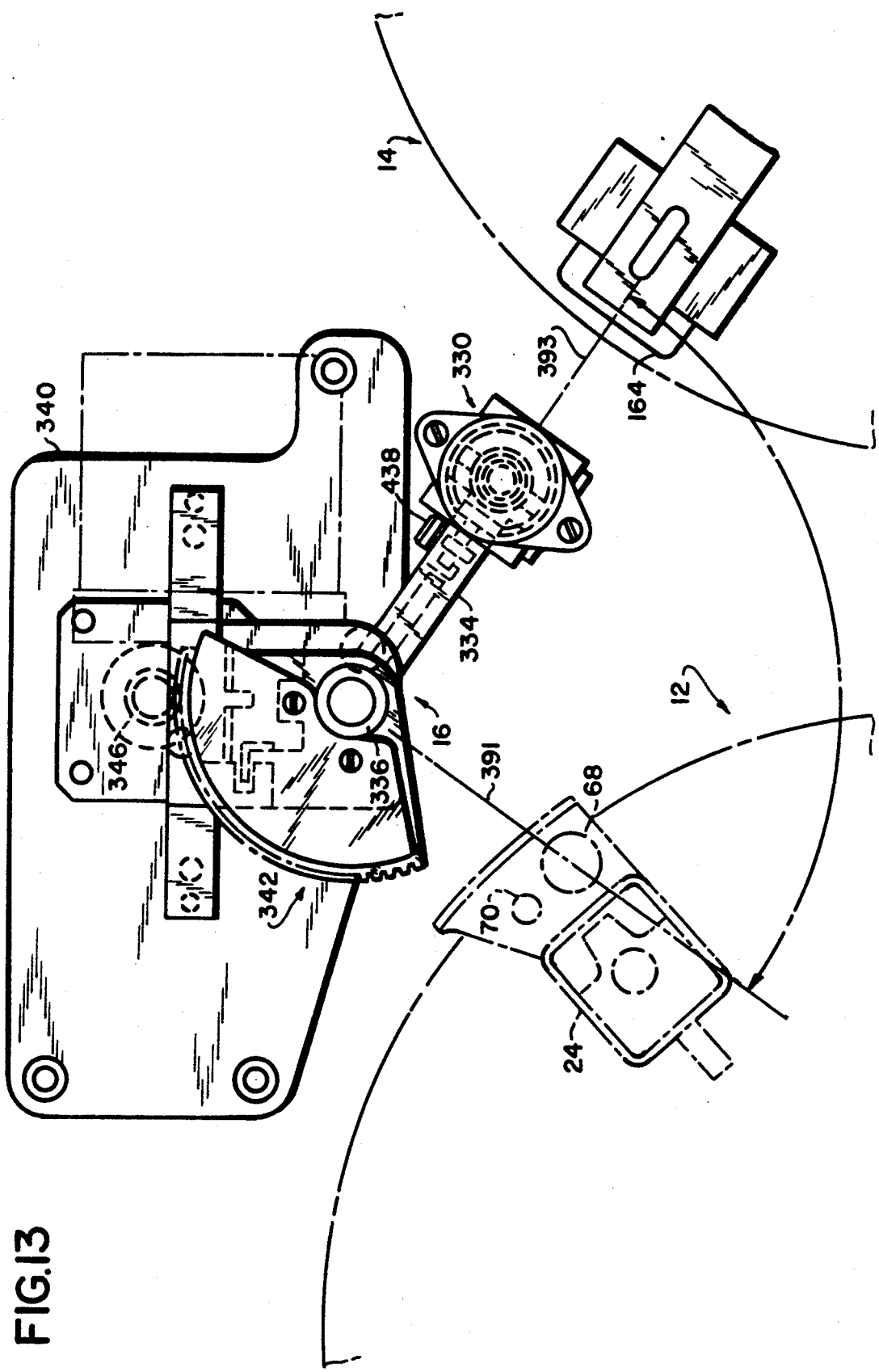
FIG. 13 is a view similar to FIG. 12 showing the range of movement of the metering module from an aspiration position to a slide spotting position.

The metering body 330 is thus capable of moving upwardly and downwardly when aligned with a slide cartridge 24 in the slide holding module 12 as shown in FIG. 12. The metering body 330 is further capable of moving upwardly and downwardly when aligned with a slide 28 held in a spotting position by the slide transfer means 18 as shown in FIG. 13. Thus the metering body 330 can be swung from an aspiration position, indicated by the centerline 391 in FIG. 13, to a spotting position, indicated by the centerline 393 in FIG. 13. In each of the aspiration and spotting positions the metering body 330 can be raised or lowered predetermined amounts.

Referring to FIGS. 8 and 9, the metering body 330 and the frame 334 are preferably formed in two mating half portions fastened together in any suitable known manner. Thus the metering body 330 comprises a front cylindrical shell portion 392 (FIG. 8) and the frame 334 comprises a front plate portion 394 extending integrally from the front shell portion 392. The metering body 330 also includes a rear cylindrical shell portion 396 (FIG. 9) and the frame 334 includes a rear plate 398 extending integrally from the rear shell portion 396.

Referring to FIG. 9, the front and rear plate portions 394 and 398 are spaced by upper and lower ribs or walls 400, 402 and side ribs or walls 404, 406.

The metering body 330 includes a pump 408 having a shaft 410 that is actuatable to protract or retract predetermined amounts in the axial direction of the shaft 410. A plunger 412 is connected to the shaft 410 via a connecting sleeve 414 that locks to the shaft 410 by a lock screw 416. The plunger 412 is joined to a swivel piece 418 that is received in a cap member 420. The cap member 420 is threaded onto the sleeve 414.

The plunger 412 is receivable in a pumping tube 422 that is joined to the metering body 330 by the threaded cap 424. A slight swivel capability of the swivel piece 418 relative to the cap 424 enables the plunger 412 to compensate for any axial misalignment between the plunger 412 and the pumping tube 422.

The pumping tube 422 is provided with an O-ring 426 to seal around the plunger 412 during axial movement of the plunger 412 by the pump shaft 410. An end portion 428 of the pumping tube 422 holds the pipette tip 70 in press-fitting relationship.

Referring again to FIG. 9, a pipette tip ejector 430 for the pipette 70 includes a cylindrical sleeve portion 432 slidably disposed on the pumping tube 422 between the pipette tip 70 and the cap 424. The pipette ejector 430 further includes a connection arm 434 detachably secured to a slide member 436 by a fastener 438. The slide member 436 is slidably disposed in the frame 334 between the metering body 330 and the side rib 406 on the rear plate 398. The slide member 436 includes an elongated slot 440 which accommodates a return spring 442. One end portion 444 of the return spring 442 is affixed to a post 446 supported in the rear plate 398. An opposite end portion 448 of the return spring 442 is affixed to the slide member 436 in a groove 449. Under normal conditions the return spring 442 maintains the slide member 436 in the position shown in FIG. 9.

The pipette tip ejector 430 further includes an actuator arm 450 pivoted at 452 such that an end portion 454 of the actuator arm 450 is confined between an end portion 456 of the slide member 436 and the upper rib 400 of the frame 334. An opposite end portion 458 of the actuator arm 446 extends toward the shaft 336. A pin 460 affixed to the shaft 336 and extending toward the metering head 330 is arranged to interfere with the end portion 458 in the manner shown in FIGS. 10 and 11 when the pinion 382 drives the rack 380 a predetermined amount toward the base plate 340.

The pipette tip ejector 430 comes into operation after all of the slides 28 in an individual cassette 24 have been removed from the cassette 24. The pipette tip 70 which is associated with the empty cassette 24 must now be removed and discarded to permit installation of a fresh new pipette tip 70 that is associated with a next sequential slide cassette 24 in the slide holding module 12.

The pipette tip 70 is ejected from the metering body 330 when the pinion 382 rotates in a counterclockwise direction as viewed in FIG. 11 to cause the rack 380 and the yoke 372 to move downwardly on the shaft 336 toward the base plate 340. Downward movement of the yoke 372 causes corresponding downward movement of the frame 334 to a downward limit position as shown in FIG. 11 wherein the pin 460 interferes with the actuator arm 450 in the manner shown in FIGS. 10 and 11.

Pivotal movement of the actuator arm 450 in a counterclockwise direction about the pivot 452 as shown in FIGS. 10 and 11, causes the end portion 454 of the actuator arm to drive the slide member 436 downwardly relative to the frame 334 and the metering body 330. Downward movement of the slide member 436 results in corresponding downward movement of the ejector sleeve 432 that surrounds the pumping tube end portion 428. The ejector sleeve 432 thus pushes the pipette tip 70 from the pumping tube end portion 428 enabling the pipette tip 70 to drop away from the pumping tube end portion 428 in the manner shown in FIG.

11. It will be noted from a comparison of FIGS. 10 and 11 that downward movement of the metering body 330 to spot a slide 28 as shown in FIG. 10 does not cause movement of the ejector 430. Movement of the ejector 430 is initiated after the metering body 330 and the frame 334 are caused to move downwardly beyond the spotting position of FIG. 10 as shown in FIG. 11.

Movements of the metering module 16 are coordinated with movements of the slide transfer device 18 as well as movements of a turntable 90 (FIG. 3) within the slide holding module 14 and the slide holding tray 146 within the incubator module 14.

At the start up of operation of the slide analysis system 10, a cartridge 24 is aligned with the external slide withdrawal slot 82 in the slide holding module 12. The metering module 16 self installs a pipette tip 70 from the slide cartridge 24 that is in the slide withdrawal position. It will be noted that all slide cartridges 24 disposed in the slide holding module 12 are equipped with corresponding pipette tips 70 and sample containers 68 that are used only for the slides within the respective slide cartridge 24.

The metering module 16 self installs the pipette tip 70 when the pinion 346 in rotated in a counterclockwise direction as viewed in FIG. 12 to cause clockwise rotation of the sector gear 342 thereby swinging the metering body 330 into alignment with the pipette tip 70 located in the cartridge 24 that is in the slide withdrawal position. The metering body 330 can thus be lowered in the manner shown in FIGS. 14-16 to cause engagement between the end portion 428 of the pumping tube 422 with the pipette tip 70. It will be noted that the free end 428 of the pumping tube 422 as shown in FIG. 14 is tapered to facilitate installation and removal of the pipette tip 70.

After the pipette tip 70 has been installed on the metering body 330 and before a first slide is spotted, the metering body is aligned by predetermined rotation of the sector gear 342 by the pinion 346 with the sample container 68. The metering head 330 is then lowered by counterclockwise engagement between the pinion 382 and the rack 380 as viewed in FIG. 9 to permit the sequence of operations represented by FIGS. 17 and 18.

With the metering body 330 in the position of FIG. 18 the pump 408 causes retraction of the shaft 410 a predetermined amount. The pump plunger 412 thus retracts a predetermined amount in the pumping tube 422 to aspirate a predetermined volume of fluid from the sample container 68 into the pipette tip 70.

As most clearly shown in FIG. 19 the amount of fluid aspirated by the pump 408 into the pipette tip 70 never exceeds a level which would cause contact between the aspirated fluid and the end portion 428 and the pumping tube 422. Thus the possibility of cross contamination between serum samples from different sample containers 68 is avoided. Furthermore the amount of dosage of serum aspirated into the pipette tip 70 is sufficient to spot one slide 28. Thus after the aspiration operation has taken place the metering body 330 elevates from the position of FIG. 18 to the position of FIG. 19 to permit movement of the metering body 330 from the aspiration position represented by the reference number 391 in FIG. 13 to the spotting position represented by the reference number 393 in FIG. 13.

With the metering body 330 located in the spotting position 393 of FIG. 13, the pump 408 causes the shaft 410 to protract a predetermined amount. Protraction of the shaft 410 causes the pump plunger 412 to protract a predetermined amount in the pump plunger 422 to dispense the aspirated serum held in the pipette tip 70 onto a slide 28. The spotted slide 28 is thus ready for insertion in the incubator module 14 by the slide engager 250 of the slide transfer device 18.

The aspiration and dispensation operations are repeated for each slide 28 contained within a slide cartridge 24.

After all slides 28 in the slide cartridge 24 have been removed by the slide transfer means 18, the pipette tip ejector 430 will initiate operation. The pinion 382 will thus rotate in a counterclockwise direction as viewed in FIG. 11 to lower the rack 380 and correspondingly lower the frame 334 to a downward limit position permitting interference between the actuator arm 450 and the pin 460 (FIGS. 10 and 11). Such interference causes shifting of the slider 436 to a downward limit position resulting in the pipette tip 70 being pushed off the pump tube end portion 428 by the ejector sleeve 432. The end portion 428 of the pumping tube is thus ready for installation of a new pipette tip 70 in the manner shown in FIGS. 14-16.

Some advantages of the present invention evident from the foregoing description include a multi-function metering or spotting device. The spotting device has a self-contained pipette tip ejector and can swivel from a pipette tip installation position to a sampling position where serum is withdrawn from a sample container to a spotting position wherein serum is dispensed onto a slide to a pipette tip ejection position wherein a used pipette tip is removed and discarded.

In view of the above, it will be seen that the several objects of the invention are achieved and other advantageous results attained.

As various changes can be made in the above constructions and methods without departing from the scope of the invention, it is intended that all matter contained in the above description or shown in the accompanying drawings shall be interpreted as illustrative and not in a limiting sense.

What is claimed is:

1. A depositing device for depositing fluid onto a slide comprising,
   (a) a dispenser housing including a tubular member having an end portion extending from said housing,
   (b) a frame joined to said dispenser housing,
   (c) a pipette tip detachably secured to the end portion of said tubular member,
   (d) means cooperable with said tubular member for drawing fluid into said pipette tip and for expelling the drawn in fluid from said pipette tip,
   (e) means for raising and lowering said dispenser housing,
   (f) means for swivelling said dispenser housing to selectable predetermined angular positions with respect to a central axis, and
   (g) pipette tip ejector means on said dispenser housing engageable with said pipette tip for separating said pipette tip from the end portion of said tubular member, including a movable member movable with said frame and said dispenser housing to a first limit position, said movable member being movable in a first direction with respect to said frame and said dispenser housing after said frame moves from said first limit position to a second limit position, and wherein said movable member urges said pipette tip away from the end portion of said tubular member responsive to movement of said frame from said first limit position to said second limit position.

2. The depositing device as claimed in claim 1 wherein said frame is mounted on a shaft defining said central axis, said frame being raised and lowered on said shaft by said raising and lowering means, said pipette tip ejector means including an engaging member fixed to one of said shaft and said frame, and a lever pivoted to the other of said shaft and said frame, for interference with said engaging member when said frame is moved to said first limit position.

3. The depositing device as claimed in claim 2 wherein said engaging member and said lever remain in interfering relationship when said frame moves beyond said first limit position to said second limit position and wherein said interference between said engaging member and said lever causes said movable member to move relative to said dispenser housing to urge said pipette tip away from the end portion of said tubular member as said frame moves from said first limit position to said second limit position.

4. The depositing device as claimed in claim 2 wherein said engaging member is provided on said shaft and said lever is pivoted to said frame.

5. The depositing device as claimed in claim 1 including means for automatically retracting said movable member in a second direction opposite said first direction as said frame moves from said second limit position back to said first limit position.

6. The depositing device as claimed in claim 5 wherein said retraction means includes a retraction spring connected to said frame and said movable member.

7. The depositing device as claimed in claim 1 wherein said frame is mounted on a shaft defining said central axis, and further including rack means cooperable with said frame and said shaft for raising and lowering said frame and dispenser housing with respect to said shaft and gear means cooperable with said shaft for swivelling said frame and said dispenser housing about said central axis.

* * * * *